United States Patent [19]

Kubota et al.

[11] Patent Number: 4,767,616
[45] Date of Patent: Aug. 30, 1988

[54] RESIN COMPOSITIONS HAVING HAIR-CONDITIONING PROPERTY

[75] Inventors: Ikuo Kubota, Tokyo; Kazuhide Hayama; Kanji Narazaki, both of Mie, all of Japan

[73] Assignee: Mitsubishi Yuka Fine Chemicals Co., Ltd., Tokyo, Japan

[21] Appl. No.: 858,646

[22] Filed: May 2, 1986

[30] Foreign Application Priority Data

May 10, 1985 [JP] Japan .................................. 60-99350

[51] Int. Cl.$^4$ ............................................ A61K 7/075
[52] U.S. Cl. ......................................... 424/70; 424/81
[58] Field of Search ................................... 424/70, 81

[56] References Cited

U.S. PATENT DOCUMENTS

| | | |
|---|---|---|
| 3,026,250 | 3/1962 | Coyner et al. |
| 3,934,595 | 1/1976 | Madrange Nee Dermain et al. |
| 3,990,459 | 11/1976 | Papantoniou .................... 424/81 X |
| 4,015,612 | 4/1977 | Pavlik et al. |
| 4,030,512 | 6/1977 | Papantoniou et al. |
| 4,075,131 | 2/1978 | Sterling ............................. 424/78 X |
| 4,358,567 | 11/1982 | Hayama et al. |
| 4,520,008 | 5/1985 | Ando et al. ....................... 424/70 X |
| 4,521,404 | 6/1985 | Lorenz et al. .................... 424/81 X |

FOREIGN PATENT DOCUMENTS

| | | |
|---|---|---|
| 286504 | 12/1970 | Austria . |
| 51-009732 | 1/1976 | Japan . |
| 104209 | 8/1980 | Japan ............................... 424/81 |
| 55-116800 | 9/1980 | Japan . |
| 56-92809 | 7/1981 | Japan . |
| 57-48335 | 3/1982 | Japan . |
| 60-25906 | 2/1985 | Japan . |
| 60-36571 | 2/1985 | Japan . |
| 60-174708 | 9/1985 | Japan . |
| 1031540 | 6/1966 | United Kingdom . |

Primary Examiner—John E. Kittle
Assistant Examiner—Susan S. Rucker
Attorney, Agent, or Firm—Oblon, Fisher, Spivak, McClelland & Maier

[57] ABSTRACT

A hair-conditioning resin composition prepared by modifying a copolymer resin with a zwitterionizing agent is described, said copolymer resin being prepared by copolymerizing in a hydrophilic solvent a polymerizable mixture containing (A) 65-90% by weight of a polymerizable vinyl monomer having the general formula (I)

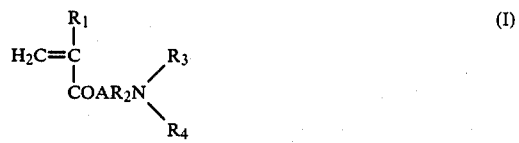

wherein $R_1$ represents a hydrogen atom or a methyl group, $R_2$ represents an alkylene group having from 1 to 4 carbon atoms, $R_3$ and $R_4$ each represents an alkyl group having from 1 to 4 carbon atoms, and A represents an oxygen atom or an NH group, (B) 10-35% by weight of polymerizable vinyl monomers having the general formula (II)

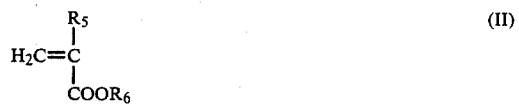

wherein $R_5$ represents a hydrogen atom or a methyl group, and $R_6$ represents a saturated or unsaturated alkyl group having from 12 to 24 carbon atoms, and (C) 0-25% by weight of other polymerizable vinyl monomers, said zwitterionizing agent having the general formula (III)

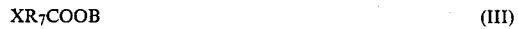

XR$_7$COOB     (III)

wherein $R_7$ represents an alkylene group having from 1 to 4 carbon atoms, X represents a bromine, chlorine or iodine atom, and B represents an alkali metal ion, an ammonium salt or an amine salt.

The hair-conditioning resin compositions of the present invention have satisfactory cosmetic properties such as voluminousness, combing-out, softening, moderately moistening, and wavesetting.

4 Claims, No Drawings

RESIN COMPOSITIONS HAVING HAIR-CONDITIONING PROPERTY

FIELD OF THE INVENTION

The present invention relates to novel hair-conditioning resin compositions having cosmetic properties such as voluminousness, combing-out, softening, moderately moistening, and wavesetting.

BACKGROUND OF THE INVENTION

It has already been proposed to use quaternary ammonium salt compounds or quaternary ammonium salt-series polymers in hair-conditioning cosmetics, such as a shampoo, a rinse, a hair treatment, a wavesetting lotion, etc., as disclosed in U.S. Pat. Nos. 3,934,595; 4,030,512; 3,836,537 and 4,075,131, and Japanese Patent Publication Nos. 11128/80 and 17009/80.

As the quaternary ammonium salt compounds, are known stearyl-trimethylammonium chloride, lauryl-trimethylammonium chloride, distearyl-dimethylammonium chloride, etc. As the quaternary ammonium salt-series polymers, are known dimethylaminoethyl methacrylate-series quaternary ammonium salt polymers, diallyl-dimethylammonium chloride-series polymers, cationic celluloses, etc.

The quaternary ammonium salt compounds have the double advantage of making the hair easier to comb and of softening it. However, the cmpounds have the disadvantage of losing the voluminousness of the hair, of losing the settlement of the hair and of making it more difficult to set. The quaternary ammonium salt-series polymers have the advantage of making the hair easier to comb. However, the polymers have the disadvantage of giving a specific malaise to the hair, that is, losing a good feeling caused by the accumulation of the polymers onto the hair in the repetitious use thereof as a so-called build-up problem. Furthermore, these quaternary ammonium salt compounds and polymers have other disadvantages in compatibility with anion-charged compounds caused by the cation charge and hyperhygroscopicity of the quaternary ammonium salt group, in the feeling of the hair at high temperature and humidity, in the worsening of the hair's condition, in the rapidly losing of the wavesetting property, etc.

On the other hand, although being useful for setting the hair, the zwitterionic polymers according to the prior art are not useful for conditioning hair.

After extensive investigations in order to solve the above-mentioned problems, the inventors of this application have found that a specific zwitterionic copolymer shows an excellent hair-conditioning effect.

SUMMARY OF THE INVENTION

It is therefore an object to eliminate disadvantages in the prior art.

It is another object to provide novel hair-conditioning resin compositions having cosmetic properties such as voluminousness, combing-out, softening, moderately moistening, and wave-setting.

In order to achieve the above-mentioned objects, according to an aspect of the present invention, the hair-conditioning resin composition is prepared by modifying a copolymer resin with a zwitterionizing agent, said copolymer resin being prepared by copolymerizing in a hydrophilic solvent a polymerizable mixture containing (A) 65–90% by weight of a polymerizable vinyl monomer having the general formula (I)

wherein $R_1$ represents a hydrogen atom or a methyl group, $R_2$ represents an alkylene group having from 1 to 4 carbon atoms, $R_3$ and $R_4$ each represents an alkyl group having from 1 to 4 carbon atoms, and A represents an oxygen atom or an NH group, (B) 10–35% by weight of polymerizable vinyl monomers having the general formula (II)

wherein $R_5$ represents a hydrogen atom or a methyl group, and $R_6$ represents a saturated or unsaturated alkyl group having from 12 to 24 carbon atoms, and (C) 0–25% by weight of other polymerizable vinyl monomers, said zwitterionizing agent having the general formula (III)

wherein $R_7$ represents an alkylene group having from 1 to 4 carbon atoms, X represents a bromine, chlorine or iodine atom, and B represents an alkali metal ion, an ammonium salt or an amine salt.

On occasion, the resin composition of the invention is prepared through the steps of filtrating precipitate, and purifying with ion-exchange resin.

DETAILED DESCRIPTION OF THE INVENTION (Vinyl monomers)

Monomers (I) are derivatives of acrylic acid or methacrylic acid represented by the above-mentioned general formula (I). Hereinafter, both the acrylic acid and methacrylic acid are generally referred to as "(meth)acrylic acid". In the above-mentioned formulae (I) through (III), $R_1$–$R_7$, A and B represent substituents as defined above, and particularly, it is preferred that $R_1$ is a methyl group, $R_2$ is an alkyl group having 2 to 3 carbon atoms, $R_3$ and $R_4$ each is a methyl group or an ethyl group, and A is an oxygen atom. Examples of preferred Monomers (I) include dimethylaminoethyl (meth)acrylate, dimethylamino-propyl (meth)acrylate, diethylamino-ethyl (meth)acrylate, dimethylamino-ethyl (meth)acrylamide, diethylamino-propyl (meth)acrylamide, etc.

The proportion of Monomer (I) to the total monomers is 65–90% by weight, and preferably, 70–85% by weight. If the proportion is less than 65% by weight, the resulting zwitterionic copolymer films become hard, thereby making the hair stiff, making it more difficult to comb the hair, and losing the moisture of the hair. If the proportion exceeds 90% by weight, the resulting copolymer films become tacky, thereby making the hair heavy and losing the voluminousness and settlement of the hair.

Monomers (II) are (meth)acrylic esters represented by the above-mentioned general formula (II). In the formula, it is generally preferred that $R_5$ is a methyl group and $R_6$ is an alkyl group having 16 to 20 carbon atoms.

If $R_6$ is an alkyl group having carbon atoms less than 12, the resulting zwitterionic copolymer films become hard, thereby making the hair stiff, making it more difficult to comb the hair and losing the moisture of the hair. Examples of Monomers (II) include palmityl (meth)acrylate, stearyl (meth)acrylate, oleyl (meth)acrylate, myristyl (meth)acrylate, behenyl (meth)acrylate, etc.

The proportion of Monomers (II) to the total monomers is 10–35% by weight, and preferably, 15–30% by weight. If the proportion is less than 10% by weight, the resulting copolymer films become tacky, thereby making the hair heavy and losing the voluminousness and settlement of the hair. If the proportion exceeds 35% by weight, the resulting copolymer films become hard, thereby making the hair stiff, giving a malaise to the hair, and making it more difficult to comb the hair.

Other vinyl monomers can be added to the Monomers (I) and (II) in order to give moderate hardness and flexibility to the resulting films in accordance with necessity. Examples of the other vinyl monomers include methyl (meth)acrylate, isobutyl (meth)acrylate, cyclohexyl (meth)acrylate, 2-ethylhexyl (meth)acrylate, acrylonitrile, acrylamide, styrene, vinyl acetate, hydroxyethyl (meth)acrylate, (meth)acrylic ester of polyethylene glycol or polypropylene glycol, N-vinyl-pyrrolidone, etc. The proportion of those other vinyl monomers to the total monomers is 0–25% by weight.

(Modifying Agent)

Specific examples of the zwitterionizing agent represented by the above-mentioned general formula (III) include sodium monobromoacetate, potassium monochloroacetate, lithium monochloropropionate, neutralized with monochloroacetic acid and ammonia, 2-amino-2-methyl-1-propanol, triethanolamine or 2-mino-2-ethyl-1,3-propanediol, etc.

The proportion of the zwitterionizing agent to Monomer (I) (or the sum amount of Monomer (I) and other monomers in the case that the other monomers contain nitrogen atoms to be zwitterionized) is 0.7–1.3, preferably 0.8–1.2, mol per mol of Monomer (I) and/or the other monomers.

(Copolymerization)

The above-mentioned Monomers (I) and (II) and other monomers are copolymerized in a hydrophilic solvent. The term "hydrophilic solvent" used herein means an organic solvent having solubility of 10 [g/100 g water/25° C.]or more in water. Preferred examples of the hydrophilic organic solvent used in the present invention include methanol, ethanol, isopropanol, ethylene glycol, ethylcellosolve, dioxane, methyl acetate, dimethylformamide, etc. The hydrophilic organic solvent may be in the hydrous state as long as no trouble occurs during polymerization, filtration and the like. An example of the hydrous organic solvent is 95% ethanol.

Copolymerization is carried out by a conventional solution polymerizing method, for example, comprising the steps of dissolving the monomers in the solvent, adding an initiator thereto, and heating the mixture with stirring under nitrogen stream. Preferred examples of the initiator include peroxides, such as benzoyl peroxide, lauroyl peroxide, etc., and azo compounds, such as azo-bis-isobutyronitrile, etc.

The copolymerization may be carried out at once in the presence of all the kinds and amounts of monomers or may be carried out partially and progressive as to the kinds and/or amounts of all the monomers.

It is preferred that the solvent is used in the amount to adjust the concentration of the resulting copolymer solution to be within a range from about 30 to about 70% by weight.

The polymerization conditions of the method of introducing the monomers and initiator, the amount of the solvent used, etc., are suitably selected. It is, however, preferred that the conditions are determined so that the resulting copolymer is made to have a numerical average molecular weight of from 30,000 to 500,000.

The zwitterionizing reaction can be carried out through the steps of adding a hydrophilic solvent solution or suspension of the zwitterionizing agent impartially or partially to the copolymer solution after the polymerization, and heating at a temperature of from about 70 to about 90° C. for a time of from about 4 to about 12 hours with suitably stirring in an inactive atmosphere, for example, in a flow of nitrogen gas.

(Purification)

In the case where B in the above-mentioned general formula (III) is alkali metal such as sodium, potassium, lithium or the like, inorganic salt (BX) is precipitated with the progression of the zwitterionizing reaction. The precipitated inorganic salt is removed. To remove the precipitated inorganic salt, any solid-liquid separation means of centrifugal separation, filtration, or the like, can be used.

The zwitterionized copolymer solution thus obtained by such means of removing the inorganic salt still may contain a little (about 0.1–about 1% by weight) of inorganic salt. To remove such a little of inorganic salt, the zwiterionized copolymer solution can be treated by batch-type or flow-type ion exchangement. In this case, the inorganic salt content can be reduced to a value of 0.1% by weight or less.

In the case where B in the above-mentioned general formula (III) is amine-series salt or ammonia salt, organic salt (BX) is not precipitated with the progression of the zwitterionizing reaction. Accordingly, the zwitterionized polymer solution can be directly used as a homogeneous solution without the steps of separating and removing BX.

The thus obtained resin can be used, in the form of a hydrophilic solvent solution, in the form of a solution in which the solvent has been removed, or in the form of a solution in which the hydrophilic solvent has been replaced by pure water, in cosmetics for hair.

The resin according to the present invention is compatibly added to the cosmetics for hair, such as a shampoo, a rinse, a hair treatment, a wavesetting lotion, or the like, in order to give the hair conditioning effects. The proportion of the resin to the cosmetics ranges from 0.01 to 5% by weight as zwitterionic polymer.

The present invention will be described hereinafter in more detail as to examples thereof.

EXAMPLE 1

70 parts by weight of dimethylamino-ethyl methacrylate, 10 parts by weight of myristyl methacrylate, 20 parts by weight of stearyl methacrylate, and 50 parts by weight of ethanol were introduced into a five neck polymerization flask, equipped with a reflux cooler, a dropping funnel, a thermometer, a glass inlet for nitrogen substitution, and a stirrer. 0.6 part by weight of α,α'-azo-bis-isobutyronitrile was added thereto and the mixture was refluxed with heating at 80° C. in a flow of nitrogen gas for 4 hours to thus carry out copolymerization.

At the end of the copolymerization, an ethanol suspension containing 40% by weight of potassium monochloroacetate equimolar with the dimethylamino-ethyl methacrylate was added to the flask, drop by drop, by means of the dropping funnel. The mixture was heated at 80° C. in a flow of nitrogen gas for 10 hours to thus carry out zwitterionizing reaction.

A precipitate was separated from the obtained viscous suspension by the use of a pressure filter (made by Nippon Dying Machine Mfg. Co., Ltd.).

The filtrate was passed through a column filled with recovered cation-exchange resin (tradename "DIAION PK-220"; in which, after recovered, the system was subject to substitution of ethanol) and then passed through a column filled with recovered anion-exchange resin (tradename "DIAION PA-416"; in which, after recovered, the system was subject to substitution of ethanol) to thus carry out purification.

The thus obtained light-yellow transparent solution was diluted with ethanol so as to adjust the copolymer resin content thereof to 30% by weight.

The thus obtained copolymer resin solution was subject to measurement of numerical average molecular weight by an osmotic pressure method (at 25° C.) by using an osmometer (made by Parkin-Elmer Inc.), and the resultant numerical average molecular weight was 300,000.

The resin ethanol solution was diluted 60 times with pure water. The diluted solution was applied to a 23 cm long and 2 g weight bundle of hair. The hair was then dried with exposed to the air. The hair-conditioning effect of the solution was excellent. (See Table 1.)

Next, 3 g of the resin ethanol solution were introduced to 100 g of an aqueous solution containing 20% by weight of alcohol sulfate sodium salt to thus obtain a shampoo-model liquid. The shampoo-model liquid was applied to a 23 cm long and 2 g weight bundle of hair. The hair was then washed with water and dried with exposed to the air. The hair-conditioning effect of the liquid was excellent. (See Table 1.)

EXAMPLES 2-4

Resin solutions were prepared in the same manner as described in Example 1 except that the monomers used in Example 1 were replaced by monomers shown in Table 1. The resulting resin solutions were then evaluated in the same manner described in Example 1. The hair-conditioning effect of the respective solution was excellent. (See Table 1.)

EXAMPLE 5

Copolymerization was carried out in the same manner as described in Example 1 except that the monomers used in Example 1 were replaced by monomers shown in Table 1. At the end of the copolymerization, an ethanol suspension containing 40% by weight of monochloroacetic acid neutralized with 2-amino-2-methyl-1-propanol equimolar with the dimethylamino-ethyl methacrylate was added to the polymerization flask, drop by drop, by means of the dropping funnel. The mixture was heated at 80° C. for 8 hours to thus carry out the zwitterionizing reaction.

The thus obtained solution was diluted with ethanol so as to adjust the resin content thereof to 30% by weight. The resulting resin solution was then evaluated in the same manner as described in Example 1. The hair-conditioning effect of the solution was excellent. (See Table 1.)

EXAMPLE 6

A resin solution was prepared in the same manner as described in Example 5 except that the monomers used in Example 5 were replaced by monomers shown in Table 1 and the zwitterionizing agent was replaced by monochloroacetic acid neutralized with triethanolamine. The resulting resin solution was then evaluated in the same manner as described in Example 1. (See Table 1.)

COMPARATIVE EXAMPLES 1-4

Resin solutions were prepared in the same manner described in Example 1 except that the monomers used in Example 1 were replaced by monomers shown in Table 2. The resulting resin solutions were then evaluated in the same manner as described in Example 1. The resin solutions were inferior in stiffness, combing-out, and so on, that is, they were unsatisfactory as hair-conditioning resin. (See Table 2.)

COMPARATIVE EXAMPLE 5

A resin solution was prepared in the same manner as described in Example 1 except that the ethanol used for the polymerization was used in the amount of 150 parts by weight. The resulting resin solution was then evaluated in the same manner as described in Example 1. The resin solution was inferior in tackiness, combing-out, and so on, that is, it was unsatisfactory as hair-conditioning resin. (See Table 2.)

Measurement of molecular weight was made on the copolymer resin in the same manner as described in Example 1. The resin had a numerical average molecular weight of 20,000.

COMPARATIVE EXAMPLE 6

70 parts by weight of dimethylamino-ethyl methacrylate, 10 parts by weight of myristyl methacrylate, 20 parts by weight of stearyl methacrylate, and 45 parts by weight of ethanol were introduced into the same flask as described in Example 1 and heated to 70° C. in a flow of nitrogen gas. A solution obtained by dissolving 0.3 part by weight of α,α'-azo-bis-isobutyronitrile into 5 parts by weight of ethanol was added to the flask having been heated to 70° C., drop by drop, for 4 hours. After the dropwise addition, the temperature was maintained at 70° C. for 3 hours to thus obtain a copolymer. After the end of the zwitterionization, the process performed in Example 1 was followed. The resulting resin solution was then evaluated in the same manner as described in Example 1. The resin solution was inferior in combing-out and stiffness, that is, it was unsatisfactory as hair-conditioning resin. (See Table 2.)

Measurement of molecular weight was made on the copolymer resin in the same manner as described in Example 1. The resin had a numerical average molecular weight of 600,000.

The performance of the respective resin shown in Tables 1 and 2 was evaluated with organolepic test and the types thereof were classified into the following three.

o: Good
Δ: Unsatisfactory
x: Very bad

TABLE 1

| Example | Composition (% by weight) Monomers (I) | | Monomers (II) | | Other Monomers | | Performance Pure water Dilution Voluminousness | Stiffness | Combing-out | Tackiness | Shampoo - Model Voluminousness | Stiffness | Combing-out | Tackiness |
|---|---|---|---|---|---|---|---|---|---|---|---|---|---|---|
| 1 | Dimethylaminoethyl methacrylate | 70 | Myristyl methacrylate<br>Stearyl methacrylate | 10<br>20 | | | o | o | o | o | o | o | o | o |
| 2 | Diethylaminoethyl methacrylate | 85 | Behenyl methacrylate | 15 | | | o | o | o | Δ | Δ | o | o | o |
| 3 | Dimethylaminopropyl acrylamide | 70 | Stearyl methacrylate | 30 | | | o | o | o | o | o | o | o | o |
| 4 | Dimethylaminoethyl methacrylate | 65 | Stearyl methacrylate | 20 | Polypropylene glycol (n = 9) methacrylic acid ester | 15 | o | Δ | o | o | o | o | o | o |
| 5 | Dimethylaminoethyl methacrylate | 70 | Stearyl methacrylate<br>Stearyl acrylate | 20<br>10 | | | o | o | o | o | o | o | o | o |
| 6 | Dimethylaminopropyl methacrylate | 75 | Behenyl methacrylate | 15 | Butyl methacrylate | 10 | o | o | o | o | o | o | o | o |

TABLE 2

| Comp. Example | Composition (% by weight) Monomers (I) | | Monomers (II) | | Other Monomers | | Performance Pure water Dilution Voluminousness | Stiffness | Combing-out | Tackiness | Shampoo - Model Voluminousness | Stiffness | Combing-out | Tackiness |
|---|---|---|---|---|---|---|---|---|---|---|---|---|---|---|
| 1 | Diethylaminoethyl methacrylate | 60 | Myristyl methacrylate<br>Lauryl methacrylate | 20<br>20 | | | o | Δ | Δ | Δ | o | o | Δ | Δ |
| 2 | Dimethylaminoethyl methacrylate | 50 | | | Methyl methacrylate<br>Isobutyl methacrylate | 25<br>25 | o | x | x | o | o | x | x | o |
| 3 | Dimethylaminopropyl methacrylate | 50 | Tridecyl methacrylate | 30 | Ethyl methacrylate | 20 | o | x | x | o | o | x | x | o |
| 4 | Dimethylaminoethyl methacrylate | 40 | Stearyl methacrylate | 20 | Polypropylene glycol (n = 9) methacrylic acid ester<br>Methyl methacrylate | 20<br>20 | o | x | x | o | o | x | x | o |
| 5 | Dimethylaminoethyl methacrylate | 70 | Myristyl methacrylate<br>Stearyl methacrylate | 10<br>20 | | | x | o | Δ | Δ | x | o | Δ | Δ |
| 6 | Dimethylaminoethyl methacrylate | 70 | Myristyl methacrylate<br>Stearyl methacrylate | 10<br>20 | | | o | x | x | o | Δ | Δ | x | o |

While the invention has been described in detail and with reference to specific embodiments thereof, it will be apparent to one skilled in the art various changes and modifications can be made therein without departing from the spirit and scope thereof.

What is claimed is:

1. A hair-conditioning resin composition prepared by modifying a copolymer resin with a zwitterionizing agent, said copolymer resin being prepared by copolymeriziing in a hydrophilic solvent a polymerizable mixture containing (A) 65–90% by weight of a polymereizable vinyl monomer having the general formula (I)

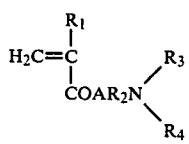

(I)

wherein $R_1$ represents a hydrogen atom or a methyl group, $R_2$ represents an alkylene group having from 1 to 4 carbon atoms, $R_3$ and $R_4$ each represents an alkyl group having from 1 to 4 carbon atoms, and A represents an oxygen atom or an NH group, (B) 10-35% by weight of polymerizable weight monomers having the general formual (II)

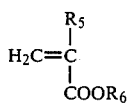

wherein $R_5$ represents a hydrogen atom or a methyl group, and $R_6$ represents a saturated or unsaturated alkyl group having from 12 to 24 carbon atoms, and (c) 0-25% by weight of other polymerizable vinyl monomers, said copolymer resin having a numerical average molecular weight of from 30,000 to 500,000, said zwitterionizing agent having the general formula (III)

$$XR_7COOB \qquad (III)$$

wherein $R_7$ represents an alkylene group having from 1 to 4 carbon atoms, X represents a bromine, chlorine or iodine atom, and B represents an alkali metal ion, an ammonium salt or an amine salt and being present in an amount of 0.7-1.3 mol per mole of monomer (I) and/or the other monomers.

2. The hair-conditiioning resin composition of claim 1, wherein said polymerizable vinyl monomer (A) having the general formula (I) is selected from a group consisting of dimethylamino-ethyl methacrylate, diethylamino-ethyl methacrylate, dimethylamino-propyl acrylamide, and dimethylamino-propyl methacrylate.

3. The hair-conditioning resin composition of claim 1, wherein said polymerizable vinyl monomer (B) having the general formula (II) is selected from a group consisting of myristyl methacrylate, stearyl methacrylate, behenyl methacrylate, and stearyl acrylate.

4. The hair-conditioning resin composition of claim 1, wherein said zwitterionizing agent having the general formula (III) is selected from a group consisting of potassium monochloroacetate, monochloroacetic acid neutralized with 2-amino-2-methyl-1-propanol, and monochloroacetic acid neutralized with triethanolamine.

* * * * *